(12) United States Patent
Spargo et al.

(10) Patent No.: US 9,327,804 B2
(45) Date of Patent: May 3, 2016

(54) BACTERIA-BASED GAS GENERATOR

(75) Inventors: Barry J Spargo, Washington, DC (US); Justin C Biffinger, Woodbridge, VA (US); Bradley R Ringeisen, Lorton, VA (US); Erinn C. Howard, Alexandria, VA (US); Lisa A. Fitzgerald, Alexandria, VA (US); Peter K Wu, Ashland, OR (US); Michael P. Malito, Washington, DC (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 1005 days.

(21) Appl. No.: 13/112,368

(22) Filed: May 20, 2011

(65) Prior Publication Data

US 2011/0229951 A1  Sep. 22, 2011

Related U.S. Application Data

(63) Continuation-in-part of application No. 12/700,759, filed on Feb. 5, 2010.

(60) Provisional application No. 61/346,530, filed on May 20, 2010, provisional application No. 61/150,446, filed on Feb. 6, 2009.

(51) Int. Cl.
| | | |
|---|---|---|
| *C12M 1/00* | (2006.01) |
| *B63B 22/18* | (2006.01) |
| *C12M 1/107* | (2006.01) |
| *C12M 1/34* | (2006.01) |
| *C12P 3/00* | (2006.01) |
| *C12P 5/00* | (2006.01) |
| *B63G 8/08* | (2006.01) |
| *B63G 8/00* | (2006.01) |

(52) U.S. Cl.
CPC ............. *B63B 22/18* (2013.01); *C12M 21/04* (2013.01); *C12M 23/36* (2013.01); *C12M 29/20* (2013.01); *C12M 41/40* (2013.01); *C12P 3/00* (2013.01); *C12P 5/00* (2013.01); *B63G 8/08* (2013.01); *B63G 2008/002* (2013.01); *Y02E 50/343* (2013.01)

(58) Field of Classification Search
CPC .......... B63B 22/18; C12P 3/00; C12M 23/36; C12M 21/04; C12M 41/40; B63G 8/08; Y02E 50/343
USPC .............................................. 435/167, 289.1
See application file for complete search history.

(56) References Cited

U.S. PATENT DOCUMENTS

| | | | |
|---|---|---|---|
| 4,270,381 A * | 6/1981 | Demaray | ....................... 73/19.1 |
| 4,374,199 A | 2/1983 | Carter | |
| 5,047,331 A | 9/1991 | Swaine et al. | |

(Continued)

OTHER PUBLICATIONS

Alshiyab et al., "Improvement of Biohydrogen Production under Increased the Reactor Size by C. acetobutylicum NCIMB 13357" American Journal of Environmental Sciences 5(1): 33-40, 2009.

(Continued)

*Primary Examiner* — Michael Hobbs
(74) *Attorney, Agent, or Firm* — US Naval Research Laboratory; Joseph T. Grunkemeyer (57) ABSTRACT

Disclosed is an apparatus having: a pressure chamber and a gas-producing microorganism within the chamber. The pressure chamber is capable of maintaining a gas pressure of at least 0.5 psi above atmospheric pressure.

18 Claims, 8 Drawing Sheets

(56) References Cited

U.S. PATENT DOCUMENTS 5,350,692 A    9/1994   Taguchi et al.
2006/0281158 A1   12/2006   Felder et al.

OTHER PUBLICATIONS

Antonopoulou et al., "Influence of pH on fermentative hydrogen production from sweet sorghum extract" International Journal of Hydrogen Energy 35 (2010) 1921-1928.
Chung, "Inhibitory Effects of H2 on Growth of Clostridium cellobioparum" Appl. And Environ. Microbiol., 31(3), 342-348 (1976).
Levin et al., "Challenges for biohydrogen production via direct lignocellulose fermentation" International Journal of Hydrogen Energy 34 (2009) 7390-7403.
Pattra et al., "Bio-hydrogen production from the fermentation of sugarcane bagasse hydrolysate by Clostridium butyricum" International Journal of Hydrogen Energy 33 (2008) 5256-5265.
Sen et al., "Status of Biological hydrogen production" J. Scientific & Industrial Res. 67 (2008) 980-993.
Zhang et al., "Biohydrogen production in a granular activated carbon anaerobic fluidized bed reactor" International Journal of Hydrogen Energy 32 (2007) 185-191.
Zhang et al., "Biological hydrogen production by Clostridium acetobutylicum in an unsaturated flow reactor" Water Research 40 (2006) 728-734.

\* cited by examiner

BACTERIA-BASED GAS GENERATOR

This application claims the benefit of U.S. Provisional Application No. 61/346,530, filed on May 20, 2010. This application is a continuation-in-part application of pending U.S. patent application Ser. No. 12/700,759, filed on Feb. 5, 2010, which claims the benefit of U.S. Provisional Application No. 61/150,446, filed on Feb. 6, 2009. These applications and all other publications and patent documents referred to throughout this nonprovisional application are incorporated herein by reference.

TECHNICAL FIELD

The present disclosure is generally related to the generation and containment of gas from microorganisms.

BRIEF SUMMARY

Disclosed herein is an apparatus comprising: a pressure chamber and a gas-producing microorganism within the chamber. The pressure chamber is capable of maintaining a gas pressure of at least 0.5 psi above atmospheric pressure.

BRIEF DESCRIPTION OF THE DRAWINGS

A more complete appreciation of the invention will be readily obtained by reference to the following Description of the Example Embodiments and the accompanying drawings.

DETAILED DESCRIPTION OF EXAMPLE EMBODIMENTS

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

Disclosed herein is an apparatus and methods for repeatedly generating gas pressure from microorganisms and bacteria to greater than 30 psi. The gas may optionally be primarily composed of hydrogen, which is considered a potential large scale fuel source of the future (Misra et al., "Hydrogen Evolution on Hydrophobic Aligned Carbon Nanotube Arrays" *ACS Nano* 2009, 3(12), 3903-3908; Ye et al., "Hydrogen generation utilizing alkaline sodium borohydride solution and supported cobalt catalyst" *Journal of Power Sources* 2007, 164(2), 544-548). The apparatus may be used with *Clostridium acetobutylicum*, a bacterium known for producing hydrogen from carbohydrate sources (Alshiyab et al., "Improvement of biohydrogen production under increased the reactor size by *C. acetobutylicum* NCIMB 13357" *American Journal of Environmental Sciences* 2009, 5(1), 33-40; Zhang et al., "Biohydrogen production in a granular activated carbon anaerobic fluidized bed reactor" *International Journal of Hydrogen Energy* 2007, 32(2), 185-191). This system is not limited to solely *Clostridium* spp., but encompasses any microorganism capable of generating gas at rates that produce significant pressure from renewable biomass.

The system may extend operational durations of autonomous sensors or unmanned underwater vehicles (UUV) and also could be used for portable power supplies. Re-pressurizing gas tanks with bacteria may eliminate the need to transport tanks to external fueling stations, generate gaseous fuels on-site using biomass, and provide ballast for long-duration aquatic sensors, communication relays, and buoys. Generating pressure via bacteria may enable the production of fuels and ballast separate from fossil fuel derived methods and processes.

Figure 1:
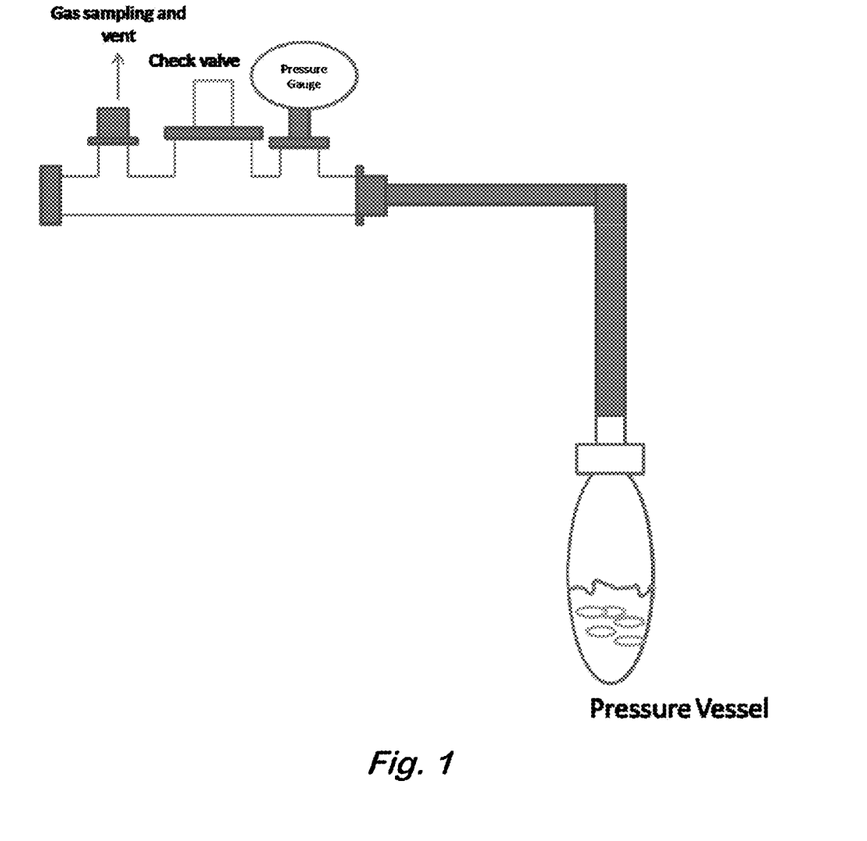
FIG. 1 shows a general schematic for a pressure chamber.

FIG. 1 shows a general schematic for a pressure chamber. The apparatus and method are based on the goal of generating pressure using bacterial gas production within a single chamber to greater than, for example, 0.5, 3, 10, or 30 psi above standard atmospheric pressure or higher. The pressure chamber may be any container generally used to contain a gas or other container that does not deform, rupture, or otherwise change its interior volume at pressures up to the operational gas pressure. The chamber could be fabricated out of glass, as well as standard non-corrosive alloys used in commercial gas tank operations The produced gas may be, for example, hydrogen, carbon dioxide, or energetic gases or gaseous fuels such as hydrocarbon gases, methane, ethane, and propane. The gas may be produced in anaerobic or aerobic conditions depending on the microorganism and the gas. The gas may be produced by a fermentative process.

Any microorganism that produces a gas may be used. Suitable hydrogen-producing microorganisms include, but are not limited to, *Clostridium* sp., *Clostridium acetobutylicum*, *Escherichia coli*, *Clostridium thermocellum*, *Clostridium cellulolyticum*, *Clostridium butyricum*, *Enterobacter aerogenes*, *Desulfovibrio vulgaris*, *Magashaera elsdenii*, *Citrobacter intermedius*, *Enterobacter cloacae*, and *Clostridium pasteurianum*. Energetic gases may be produced by, for example, *Methanocelleus bourgensis*, *Methanomicrobiales* sp., *Methanobacterium* sp., *Methanobacterium bryantii*, *Methanobacterium formicum*, *Methanopyrus kandleri*, *Methanococcus* sp., *Methanococcus jannaschii*, *Methanococcus deltae*, *Methanococcus maripaludis*, *Methanococcus vannielii*, and *Methanocelleus marisnigri*. These methane producing bacteria may also have the potential to produce smaller quantities of ethane and propane. An agar matrix may act as a growth support for the stabilization of gas generation.

The pressure chamber may be coupled to a vent that may release the gas produced by the microorganism. The vent may be an integral part of the pressure chamber or may coupled to the pressure chamber through one or more intermediate parts, such as tubing. Any form of vent may be used. The vent may automatically release gas when the pressure inside the chamber reaches a threshold level, or may release gas periodically through the use of a timer. The vent may also be opened manually or robotically at any time or based on any criteria.

When a food source appropriate for the microorganism and any desired gas are within the pressure chamber such that the microorganism can metabolize the food, the resulting gas may be allowed to build up over time to an elevated pressure. The pressure may build up to, for example, 0.5, 5, 10, or 30 psi above standard atmospheric pressure or higher. The built-up pressure or portion thereof may then be vented through the vent. The venting may be triggered by the level of the pressure in the chamber or by other criteria. The pressure may be vented back to atmospheric pressure or maintained at a higher level.

The process of building up gas pressure and venting the gas may be repeated one more times. This may continued potentially until the food source is no longer sufficient to increase the pressure. The process may continue for longer or even indefinitely by placing additional food source in the chamber. The food source may be added in batches or continuously. The food may be added through an optional food inlet.

Additional components may be incorporated with the apparatus to exploit the venting of the gas from the chamber. In one embodiment the pressure chamber is enclosed in a container having a divider or bulkhead that divides the container into a ballast chamber and a dry chamber. The vent can move gas from the pressure chamber to the dry chamber, a gas valve moves gas from the dry chamber to the ballast chamber, and a ballast valve moves liquid between the ballast chamber and the exterior of the container.

When the container is submerged in a liquid, such as water or ocean water, gas may be vented into the dry chamber and subsequently into the ballast chamber. This displaces water in the ballast chamber to the exterior, resulting in the container rising in the liquid. When the ballast container is refilled with liquid, the container sinks.

Figure 2:
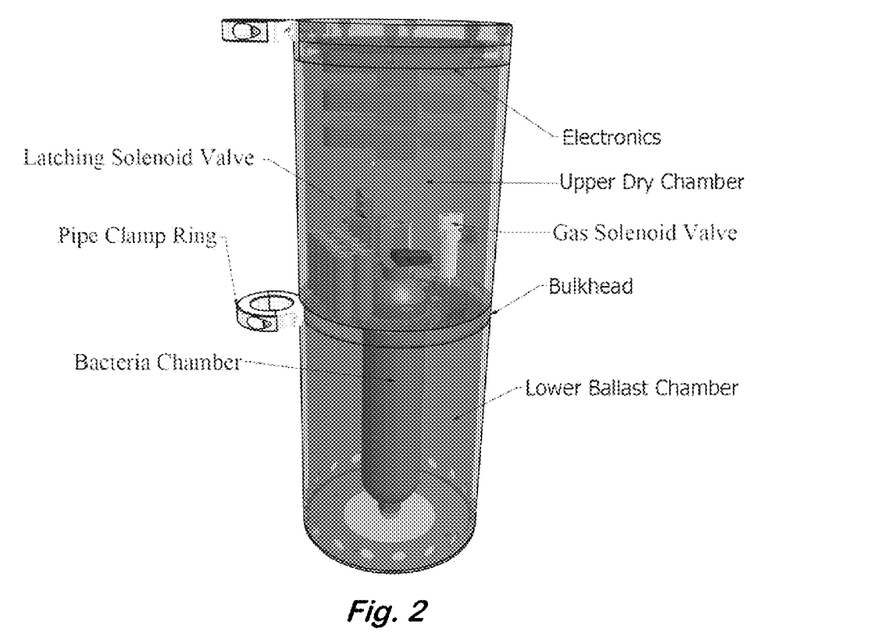
FIG. 2 shows a general schematic for autonomous floating system using pressurized bacterial ballast.

FIG. 2 schematically illustrates an example of this embodiment. The floater device has the objective of floating and sinking itself in a marine environment by utilizing gas producing bacteria.

Design Considerations for the Device Include:
1. The device should automatically rise to the surface along a tether, pause at the top and then sink again. It should be able to perform this several times per day
2. The device should resist corrosion, clogging, and the pressure of 10 meters of sea water. It should not sink into the sand or sediment of the ocean floor.
3. The gas produced by the bacteria is hydrogen. Special material will need to be utilized to minimize the leakage of hydrogen.
4. The bacterial chamber should be filled with agar in an anaerobic environment. The chamber should also permit the injection of the bacteria into the agar with a syringe and needle. The injection should be possible in the field while maintaining the anaerobic environment.
5. The valve system should use minimal power, permitting reduced battery size and increased operating time.

The example floater device (FIG. 2) is a cylinder consisting of an upper dry chamber and lower ballast chamber. The upper dry chamber contains the electronics, batteries, a gas solenoid valve, a latching solenoid valve, and a pressure data recorder. The bacterial chamber is screwed in between the two chambers and sealed with an o-ring. There are multiple fittings on the bulkhead between the two chambers that accommodates gas lines and a pressure sensor to determine the ocean depth of the floater.

The gas solenoid valve controls the flow of hydrogen into the ballast tank. The latching solenoid valve vents the ballast tank to the outside environment. This latching solenoid valve is a "pinch" type. The "pinch" type valve permits the only whetted material in the valve to be the tube. The tube may be PharMed® tubing, which holds up very well to the ocean environment.

While resting on the ocean floor, the latching solenoid valve remains in its open position. To rise, the system closes the latching valve, sealing off the ballast tank. The gas valve then briefly opens to fill the ballast tank. With its increased buoyancy, the floater rises to the surface. After a period of time at the surface, the latching solenoid valve returns to its venting state and the floater begins its decent along the tether. Two pipe clamp rings are attached to the side of the floater to guide it up and down the tether.

The bacteria chamber is stainless steel and has metal fittings at each end to prevent hydrogen leakage. The top fitting is a nickel-coated brass ball valve which permits the chamber to be filled with agar in an inert environment and then sealed off for transport. This ball valve is fitted with a HPLC fitting to mate with the bacteria tank valve.

Figure 3:
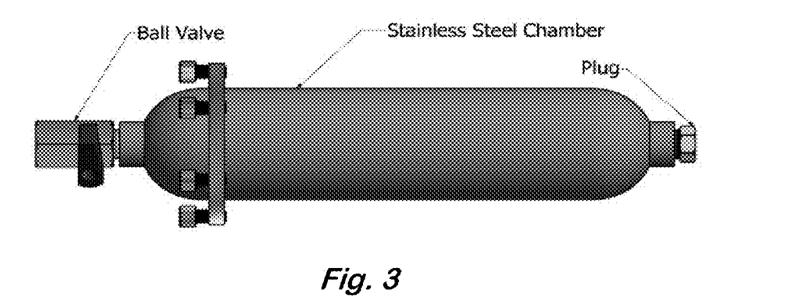
FIG. 3 shows a general design for bacterial gas tank used in autonomous floating system.

The bottom of the bacterial chamber is fitted with a stainless steel plug (FIGS. 2-3). When the agar is cast, it forms against this plug. In the field, the plug is removed and bacteria are injected directly into the agar. Forming the agar against the plug creates virtually no head space between the two. When the bacteria are injected and the plug replaced, virtually no oxygen is introduced into the chamber.

In another embodiment, the apparatus is the source of gas for use in the buoyancy control device disclosed in US Patent Application Publication No. 2010/0199907. This device has a floater chamber having a gas inlet coupled to the vent, a second gas vent, and a liquid vent; and a float and a weight coupled to the floater chamber. The float has a lower density than the floater chamber. The weight has a higher density than the floater chamber. The aggregate density of the floater chamber, the float, and the weight is greater than the density of the floater chamber. The gas inlet, the second gas vent, the liquid vent, the float, and the weight are positioned on the floater chamber such that when the floater chamber is filled with and submerged in a liquid in which the floater chamber is neutrally-buoyant, the floater chamber is oriented to place the second gas vent below the gas inlet; and when a gas is introduced through the gas inlet into the floater chamber that is filled with the liquid, the floater chamber pivots to raise the second gas vent until a portion of the gas escapes from the floater chamber through only the second gas vent.

When a portion of the gas is vented into the floater chamber, the floater chamber pivots until a portion of the gas escapes from the floater chamber through the second gas vent. After enough gas escapes, the floater chamber returns to a position at which gas does not escape from the floater chamber. This process can be repeated. Additional details may be found in US Patent Application Publication No. 2010/0199907.

Figure 4:
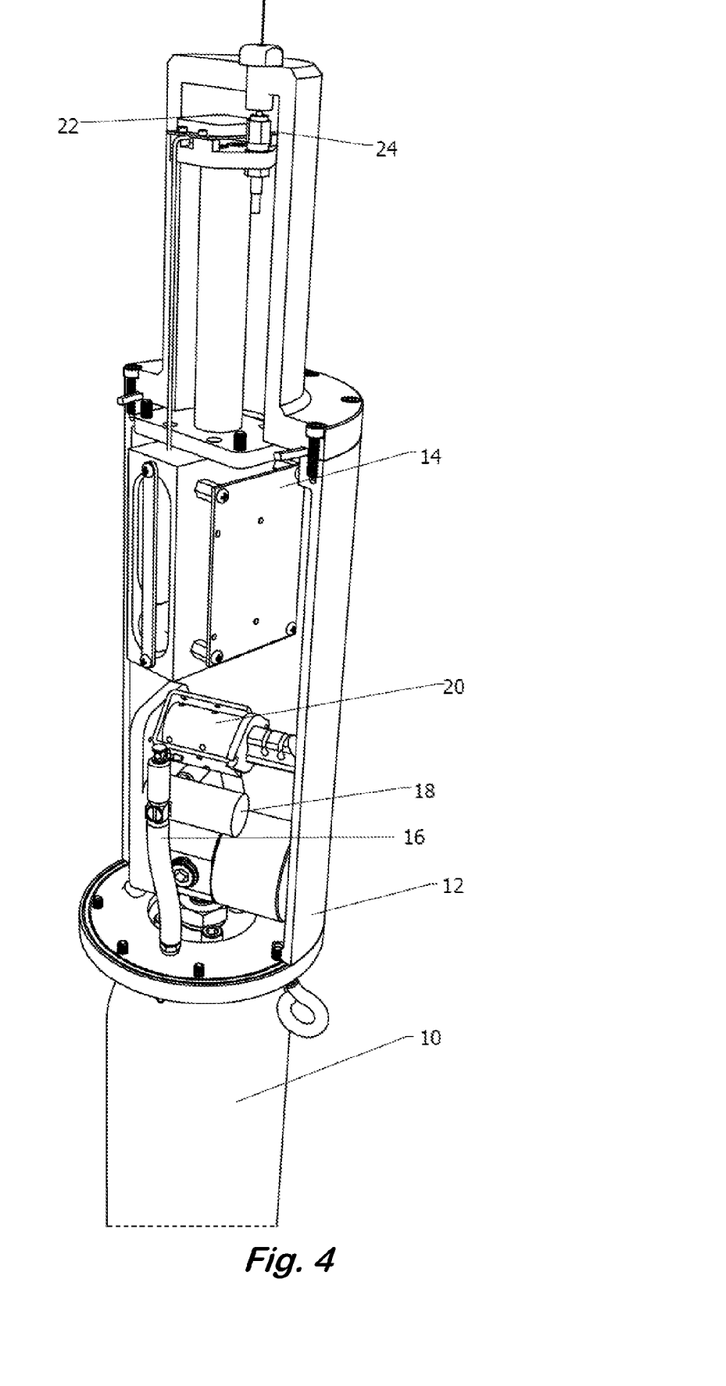
FIG. 4 shows a general schematic for a deployed sensor.
Figure 5:
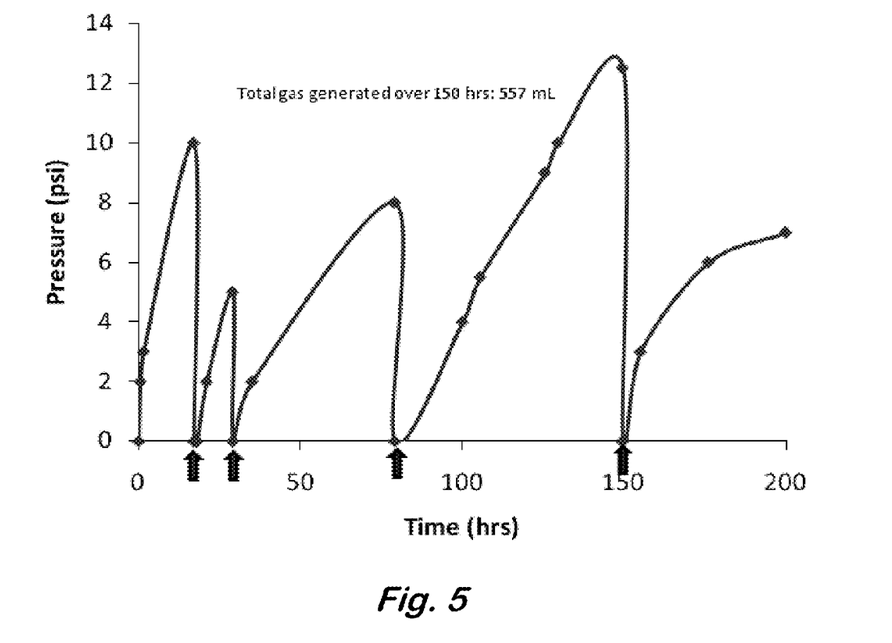
FIG. 5 shows pressure generated from *Clostridium acetobutylicum* using glucose (10% w/w) in a 11.2 g/L agar support over 200 hours at 21° C. Release of pressure is indicated by arrows. Tube was filled to 30% capacity.

An another embodiment, an inflatable bladder have a release vent is coupled to the vent. Venting gas into the bladder causes the device to rise in the liquid. Venting the bladder to the exterior cases the device to sink. In one example (FIG. 4) a pressure vessel 10 is attached to a secondary compartment 12 with all electronics 14 necessary for a deployed sensor. There is a regulator 16 attached directly to the pressure vessel 10 so that no matter what the pressure is inside the vessel, the output pressure is regulated to be less than 80 psi. There is a valve 18 attached to the regulator 16 that will release a portion of the pressure to blow up a bladder (causing a positive buoyant force) and another valve 20 attached to the bladder to release the pressure and deflate it at a later time. The bladder (not shown) surrounds the electronics container. This container may contain a GPS 22, a microchip (not shown) to process acoustic data/algorithms and to control the surfacing/sinking valves, and radio transmission 24 to a satellite.

Hydrogen generation was used for the purpose of parallel fuel synthesis in the same system. Two different agar concentrations were used for proof of principle (11.2 g/L agar (75%) and 3.8 g/L agar (25%)).

The following examples are given to illustrate specific applications. These specific examples are not intended to limit the scope of the disclosure in this application.

EXAMPLE 1

The results from the two different agar concentrations confirmed that matrices containing more liquid are less supportive of elevated pressures. An agar concentration of 11.2 g/L generated the highest pressure and, as long as agar concentration does not begin to hinder gas production or bacterial growth, higher concentrations of agar should generate higher pressures. The general experimental details are below. Pressure measurements were performed in a glass system purchased from Ace glass. The general schematic of the system is shown in FIG. 1.

Agar at 11.2 g/L concentration (75%) in Reinforced Clostridial Medium amended with 10% w/w glucose was used as the base support for growth of *Clostridium acetobutylicum* (ATCC 39236) under an inert atmosphere. In 100 mL glass 1 neck pressure tubes, 30 mL of the sterilized hot agar medium was filled. The sterilized medium was allowed to degas and cool in the anaerobic chamber. Each tube was inoculated with active *C. acetobutylicum* (determined by the formation of gas bubbles) by stabbing into the agar supports 5-7 times. Each tube was then sealed with gas tight pressure seals and connected to an analog pressure gauge. Time and pressure measurements were recorded manually. The experiment was performed at 21° C. and 35° C. (FIGS. 5-13, Tables 1-3).

The pressure that was generated reached a maximum pressure over 24 hours. The system was vented and the gas that was generated was analyzed using a Varian gas chromatograph with thermal conductivity detector (GC/TCD) calibrated for $CO_2$, $CO$, $H_2$, $CH_4$, $O_2$, and $N_2$ with a custom valve setup and packed columns (FIGS. 5-13, Tables 1-3).

TABLE 1

Figure 6:
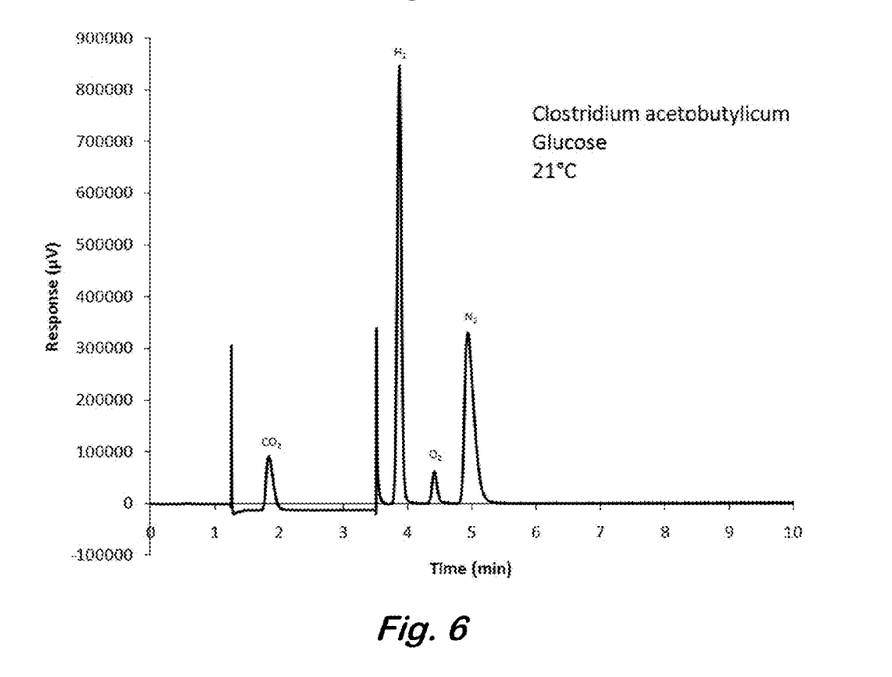
FIG. 6 shows a GC/TCD chromatograph of gas composition generated by *Clostridium acetobutylicum* from glucose (10% w/w) at 21° C. Residual oxygen and nitrogen are from the injection.
Figure 7:
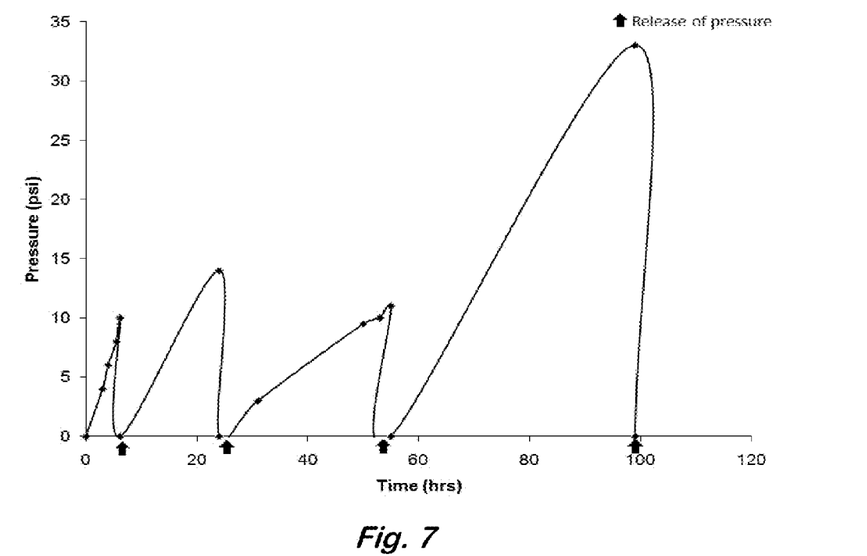
FIG. 7 shows pressure generated from *Clostridium acetobutylicum* using glucose (10% w/w) in a 11.2 g/L agar support at 35° C. Release of pressure is indicated by arrows. Tube was filled to 30% capacity.

Analytical data from GC/TCD experiment in FIG. 6

| Index | Name | Time (min) | Quantity (%) | Height (µV) | Area (µV · min) | Area % |
|---|---|---|---|---|---|---|
| 1 | $CO_2$ | 1.86 | 5.03 | 75908.4 | 9457.2 | 5.944 |
| 2 | hydrogen | 3.88 | 61.42 | 1050319.2 | 83345.5 | 52.381 |
| 3 | unknown | 4.16 | 0.00 | 1860.7 | 139.6 | 0.088 |
| 4 | oxygen | 4.42 | 4.01 | 92894.2 | 9091.9 | 5.714 |
| 5 | nitrogen | 4.94 | 29.54 | 330127.0 | 57032.2 | 35.843 |
| 6 | unknown | 10.00 | 0.00 | 1006.3 | 47.9 | 0.030 |
| Total | | | 100.00 | 1552115.8 | 159114.4 | 100.000 |

TABLE 2

Figure 8:
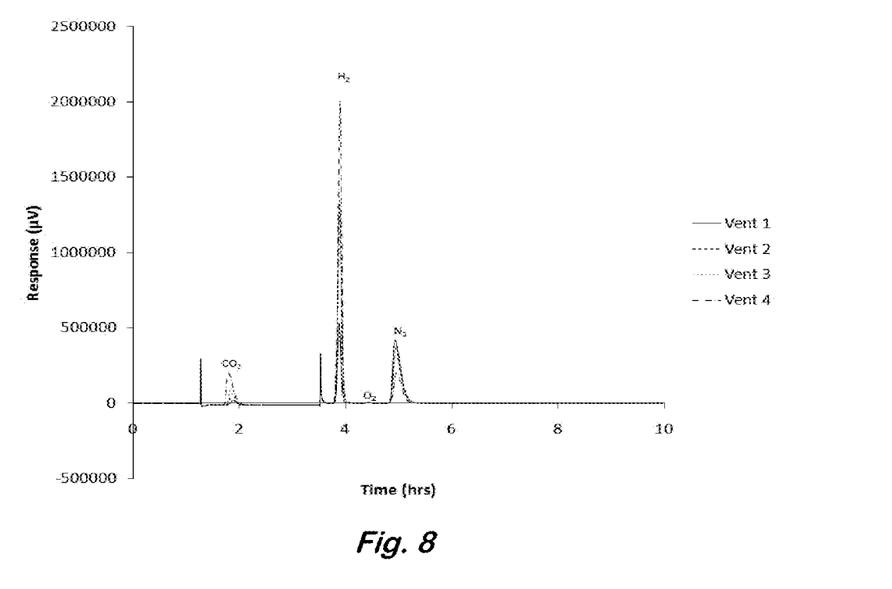
FIG. 8 shows a GC/TCD chromatograph of gas composition generated by *Clostridium acetobutylicum* from glucose (10% w/w) at 35° C. Residual oxygen and nitrogen are from the injection.
Figure 9:
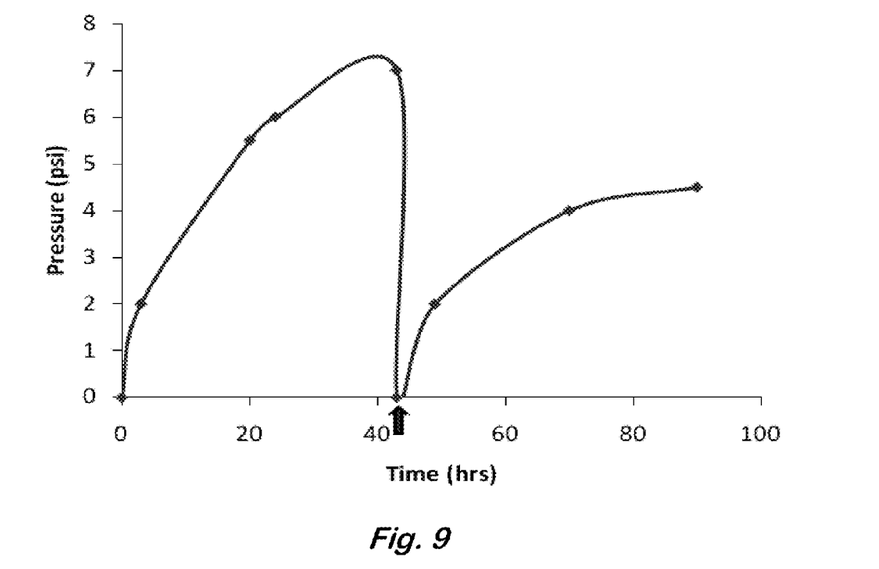
FIG. 9 shows pressure generated from *Clostridium acetobutylicum* using glucose (10% w/w) in a 3.8 g/L agar support at 21° C. Release of pressure is indicated by arrows. Tube was filled to 30% capacity.
Figure 10:
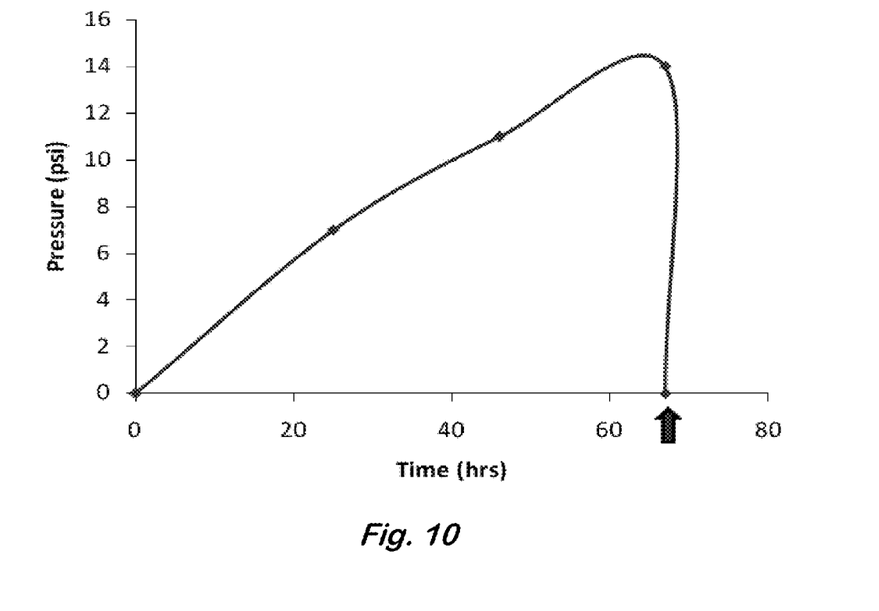
FIG. 10 shows the maximum pressure generated from *Clostridium acetobutylicum* using glucose (10% w/w) in a 11.2 g/L agar support over 65 hours at 21° C. Release of pressure is indicated by arrows. Tube was filled to 50% capacity.
Figure 11:
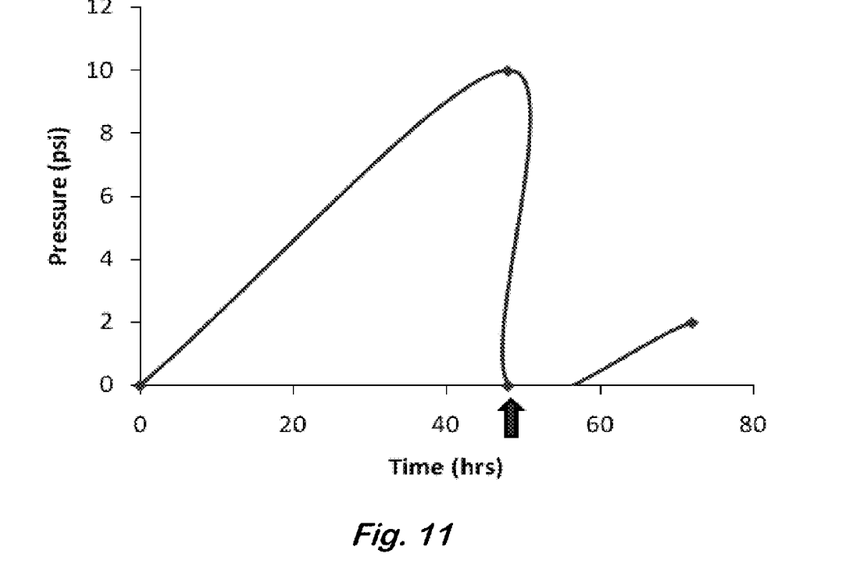
FIG. 11 shows pressure generated from *Clostridium acetobutylicum* using pectin (5% w/w) in a 11.2 g/L agar support at 35° C. Release of pressure is indicated by arrows. Tube was filled to 50% capacity.

Analytical data from GC/TCD experiment in FIG. 8

| Index | Name | Time (min) | Quantity (%) | Height (µV) | Area (µV · min) | Area % |
|---|---|---|---|---|---|---|
| Vent 1 | | | | | | |
| 1 | $CO_2$ | 1.89 | 2.73 | 75908.4 | 9457.2 | 5.944 |
| 2 | hydrogen | 3.87 | 43.44 | 1050319.2 | 83345.5 | 52.381 |
| 3 | oxygen | 4.42 | 4.01 | 92894.2 | 9091.9 | 5.714 |
| 4 | nitrogen | 4.93 | 29.54 | 330127.0 | 57032.2 | 35.843 |
| Total | | | 100.00 | 1552115.8 | 159114.4 | 100.000 |
| Vent 2 | | | | | | |
| 1 | $CO_2$ | 1.86 | 4.18 | 75195.4 | 9240.3 | 5.102 |
| 2 | hydrogen | 3.88 | 67.82 | 1344784.0 | 108211.3 | 59.753 |
| 3 | oxygen | 4.42 | 0.22 | 4890.4 | 577.0 | 0.319 |
| 4 | nitrogen | 4.94 | 27.78 | 364734.7 | 63069.4 | 34.826 |
| Total | | | 100.00 | 1789604.0 | 181098.0 | 100.000 |
| Vent 3 | | | | | | |
| 1 | $CO_2$ | 1.84 | 7.40 | 124815.8 | 16038.1 | 9.021 |
| 2 | hydrogen | 3.88 | 67.25 | 1314890.0 | 105227.0 | 59.185 |
| 3 | oxygen | 4.42 | 0.25 | 5567.7 | 657.0 | 0.370 |
| 4 | nitrogen | 4.94 | 25.10 | 322473.3 | 55872.4 | 31.425 |
| Total | | | 100.00 | 1767747.0 | 177794.5 | 100.000 |

TABLE 3

Figure 12:
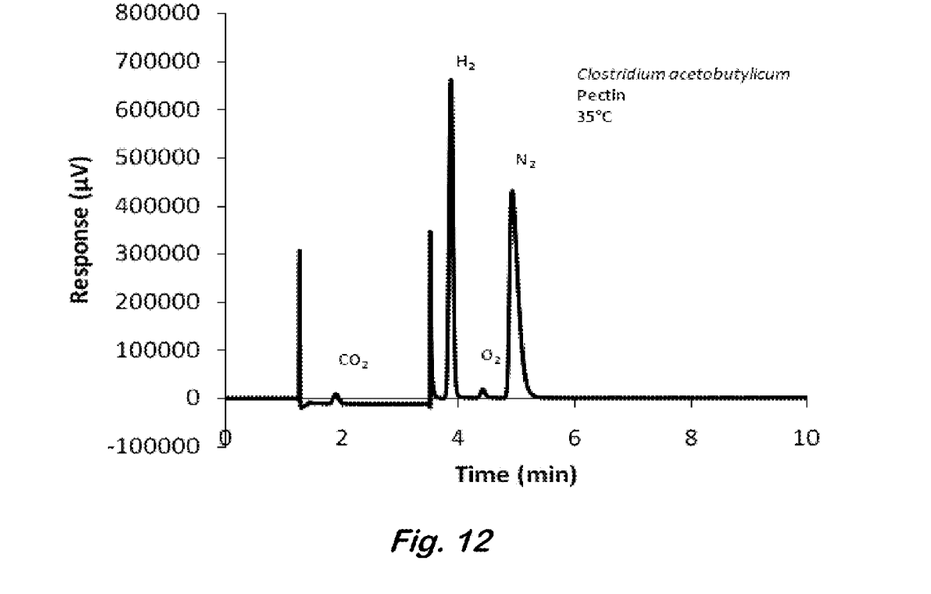
FIG. 12 shows a GC/TCD chromatograph of gas composition generated by *Clostridium acetobutylicum* from pectin (5% w/w) at 35° C. Residual oxygen and nitrogen are from the injection.
Figure 13:
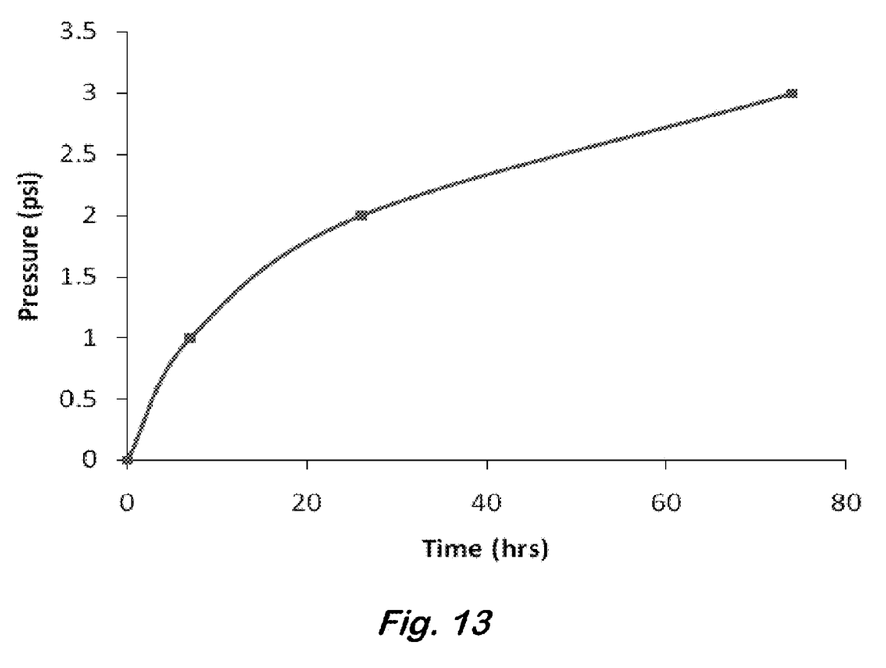
FIG. 13 shows pressure generated from *Clostridium acetobutylicum* using pectin (5% w/w) in a 11.2 g/L agar support at 21° C. Release of pressure is indicated by arrows. Tube was filled to 50% capacity.

Analytical data from GC/TCD experiment in FIG. 12

| Index | Name | Time (min) | Quantity (%) | Height (µV) | Area (µV · min) | Area % |
|---|---|---|---|---|---|---|
| 1 | $CO_2$ | 1.89 | 1.53 | 19816.1 | 2291.5 | 1.734 |
| 2 | hydrogen | 3.87 | 48.40 | 662526.2 | 52400.1 | 39.659 |
| 3 | oxygen | 4.42 | 1.03 | 18273.9 | 1865.7 | 1.412 |
| 4 | unknown | 4.65 | 0.00 | 646.2 | 17.6 | 0.013 |
| 5 | nitrogen | 4.93 | 49.04 | 431644.4 | 75539.0 | 57.172 |
| 6 | unknown | 7.95 | 0.00 | 284.6 | 11.5 | 0.009 |
| Total | | | 100.00 | 1133191.4 | 132125.4 | 100.000 |

EXAMPLE 2

Due to the possibility of bacterial death due to exposure of the bacterial cells to high levels of pressure (thereby creating an unsustainable ballast system), *C. acetobutylicum* cell viability was tested under varying pressures. *C. acetobutyli-*

*cum* cells were grown in Reinforced Clostridial Medium at an 11.2 g/L agar concentration amended with 10% w/w glucose. Cells were then subjected to different pressures (0, 5, 10, 20, and 30 psi) and stained with a live/dead bacterial stain (Invitrogen LIVE/DEAD BacLight kit) to determine the viability of cells following exposure to pressures. Showing the live/dead stain works properly, cells intentionally killed in 30% $H_2O_2$ were stained and found to be 100% dead, while cells at 0 psi (presumed to be mostly live) were stained and indeed found to be alive at a reasonable proportion to dead cells. The other pressures (5, 10, 20, 30 psi) showed the same proportion of live/dead cells as at 0 psi indicating that pressure does not decrease cell viability and that the ballast system is indeed sustainable.

Obviously, many modifications and variations are possible in light of the above teachings. It is therefore to be understood that the claimed subject matter may be practiced otherwise than as specifically described. Any reference to claim elements in the singular, e.g., using the articles "a," "an," "the," or "said" is not construed as limiting the element to the singular.

What is claimed is:

1. An apparatus comprising:
a pressure chamber;
a gas-producing microorganism within the chamber;
wherein the pressure chamber is capable of maintaining a gas pressure of at least 0.5 psi above atmospheric pressure;
a vent coupled to the pressure chamber configurable to allow the gas pressure in the chamber to increase and configurable to release gas produced by the microorganism;
a container enclosing the pressure chamber;
a divider within the container dividing the container into a ballast chamber and a dry chamber;
wherein the vent is configured to move gas from the pressure chamber to the dry chamber;
a gas valve configured to move gas from the dry chamber to the ballast chamber; and
a ballast valve configured to move liquid between ballast chamber and the exterior of the container.

2. The apparatus of claim 1, wherein the microorganism is a fermentative gas-producing microorganism.

3. The apparatus of claim 1, wherein the microorganism is a hydrogen-, methane- or carbon dioxide-producing microorganism.

4. The apparatus of claim 1, wherein the microorganism is *Clostridium* sp. or *Clostridium acetobutylicum.*

5. A method comprising:
providing the apparatus of claim 1;
placing a food source for the microorganism within the pressure chamber; and
allowing the gas pressure in the pressure chamber to increase to at least 0.5 psi above atmospheric pressure.

6. A method comprising:
providing the apparatus of claim 1;
wherein the pressure chamber is capable of maintaining a gas pressure of at least 10 psi above atmospheric pressure;
placing a food source for the microorganism within the pressure chamber; and
allowing the gas pressure in the pressure chamber to increase to at least 10 psi above atmospheric pressure.

7. The method of claim 5, further comprising:
venting a portion of the gas through the vent.

8. The method of claim 7, further comprising:
repeating allowing the gas pressure to increase and venting a portion of the gas one or more times.

9. A method comprising:
submerging the apparatus of claim 1 in a liquid;
wherein a food source for the microorganism is within the pressure chamber;
allowing the gas pressure in the pressure chamber to increase to at least 0.5 psi above atmospheric pressure;
venting a portion of the gas through the vent and into the dry chamber; and
moving a portion the gas in the dry chamber through the gas valve and into the ballast chamber, such that a portion of the liquid in the ballast chamber moves to the exterior of the container and the container rises.

10. The method of claim 9, further comprising:
moving the liquid from the exterior of the container into the ballast chamber such that the container sinks.

11. The method of claim 9;
wherein the pressure chamber is capable of maintaining a gas pressure of at least 10 psi above atmospheric pressure; and
wherein the gas pressure in the pressure chamber is allowed to increase to at least 10 psi above atmospheric pressure.

12. An apparatus comprising:
a pressure chamber;
a gas-producing microorganism within the chamber;
wherein the pressure chamber is capable of maintaining a gas pressure of at least 0.5 psi above atmospheric pressure;
a vent coupled to the pressure chamber configurable to allow the gas pressure in the chamber to increase and configurable to release gas produced by the microorganism;
a floater chamber having a gas inlet coupled to the vent, a second gas vent, and a liquid vent; and
a float and a weight coupled to the floater chamber;
wherein the float has a lower density than the floater chamber;
wherein the weight has a higher density than the floater chamber;
wherein the aggregate density of the floater chamber, the float, and the weight is greater than the density of the floater chamber; and
wherein the gas inlet, the second gas vent, the liquid vent, the float, and the weight are positioned on the floater chamber such that:
when the floater chamber is filled with and submerged in a liquid in which the floater chamber is neutrally-buoyant, the floater chamber is oriented to place the second gas vent below the gas inlet; and
when a gas is introduced through the gas inlet into the floater chamber that is filled with the liquid, the floater chamber pivots to raise the second gas vent until a portion of the gas escapes from the floater chamber through only the second gas vent.

13. A method comprising:
submerging the apparatus of claim 12 in a liquid;
wherein the a food source for the microorganism is within the pressure chamber;
allowing the gas pressure in the pressure chamber to increase to at least 0.5 psi above atmospheric pressure;
venting a portion of the gas through the vent and into the floater chamber;

allowing the floater chamber to pivot until a portion of the gas escapes from the floater chamber through the second gas vent; and allowing the floater chamber to return to a position at which gas does not escape from the floater chamber.

14. The method of claim 13;
wherein the pressure chamber is capable of maintaining a gas pressure of at least 10 psi above atmospheric pressure; and
wherein the gas pressure in the pressure chamber is allowed to increase to at least 10 psi above atmospheric pressure.

15. An apparatus comprising:
a pressure chamber;
a gas-producing microorganism within the chamber;
wherein the pressure chamber is capable of maintaining a gas pressure of at least 0.5 psi above atmospheric pressure;
a vent coupled to the pressure chamber configurable to allow the gas pressure in the chamber to increase and configurable to release gas produced by the microorganism; and
an inflatable bladder having a release vent coupled to the vent.

16. A method comprising:
submerging the apparatus of claim 15 in a liquid;
wherein a food source for the microorganism is within the pressure chamber;
allowing the gas pressure in the pressure chamber to increase to at least 0.5 psi above atmospheric pressure;
venting a portion of the gas through the vent and into the bladder.

17. The method of claim 16, further comprising:
venting gas from the bladder to the exterior of the container and the bladder.

18. A method comprising:
submerging the apparatus of claim 15 in a liquid;
wherein the pressure chamber is capable of maintaining a gas pressure of at least 10 psi above atmospheric pressure; and
wherein a food source for the microorganism is within the pressure chamber;
allowing the gas pressure in the pressure chamber to increase to at least 10 psi above atmospheric pressure; and
venting a portion of the gas through the vent and into the bladder.

* * * * *